(12) United States Patent
Burton et al.

(10) Patent No.: US 8,985,105 B2
(45) Date of Patent: Mar. 24, 2015

(54) APPARATUS FOR DELIVERY OF PRESSURISED GAS

(75) Inventors: David Burton, Camberwell (AU); Fred Blochlinger, Mount Eliza (AU); Warwick Freeman, Abbotsford (AU); Grant Parratt, Abbotsford (AU); Allan Wallace, Tranmere (AU)

(73) Assignee: Compumedics Medical Innovation Pty Ltd, Abbotsford, Victoria (AU)

( * ) Notice: Subject to any disclaimer, the term of this patent is extended or adjusted under 35 U.S.C. 154(b) by 1351 days.

(21) Appl. No.: 12/091,060

(22) PCT Filed: Oct. 16, 2006

(86) PCT No.: PCT/AU2006/001513
§ 371 (c)(1),
(2), (4) Date: Apr. 24, 2009

(87) PCT Pub. No.: WO2007/045017
PCT Pub. Date: Apr. 26, 2007

(65) Prior Publication Data
US 2009/0301482 A1   Dec. 10, 2009

(30) Foreign Application Priority Data
Oct. 21, 2005  (AU) .............................. 2005905836

(51) Int. Cl.
*F16K 31/02*   (2006.01)
*F04B 49/06*   (2006.01)
*H02K 29/08*   (2006.01)
(Continued)

(52) U.S. Cl.
CPC ............ *A61M 16/10* (2013.01); *A61M 16/1075* (2013.01); *A61M 16/16* (2013.01); *A61M 16/0069* (2013.01); *A61M 16/109* (2013.01); *A61M 2016/0027* (2013.01);
(Continued)

(58) Field of Classification Search
USPC ............. 128/200.24, 203.12, 203.16, 203.17, 128/203.26, 204.18, 204.21, 204.23; 417/22, 45; 416/44; 318/768, 721, 318/400.37–400.4, 400.32–400.36
See application file for complete search history.

(56) References Cited

U.S. PATENT DOCUMENTS 5,265,594 A   11/1993   Olsson et al.
5,380,267 A   1/1995    Boutelle et al.
(Continued)

FOREIGN PATENT DOCUMENTS

DE   20213232 U1   3/2003
EP   1110573 A2    6/2001
(Continued)

*Primary Examiner* — Lynne Anderson
*Assistant Examiner* — Bradley Philips
(74) *Attorney, Agent, or Firm* — Scott H. Davison; Procopio, Cory, Hargreaves & Savitch LLP

(57) ABSTRACT

The present invention provides a gas delivery device and system and methods for delivering humidified pressurized gas through a conduit to a subject. The configuration of the elements of the gas delivery device enable the device to be conveniently oriented from a horizontal to vertical position to suit the needs of a user. The gas delivery device may incorporate a Helmholtz resonator for dampening sound of the motor. The conduit may incorporate concentric tubes to allow it to conveniently engage the humidifier at a single aperture. The invention includes a method of operating a blower motor for a gas delivery device using a single Hall sensor.

3 Claims, 14 Drawing Sheets

(51) Int. Cl.
*A61M 16/10* (2006.01)
*A61M 16/16* (2006.01)
*A61M 16/00* (2006.01)

(52) U.S. Cl.
CPC ... *A61M 2016/0039* (2013.01); *A61M 2205/42* (2013.01); *A61M 2205/505* (2013.01)
USPC .................. 128/204.21; 417/45; 318/400.38

(56) References Cited

U.S. PATENT DOCUMENTS

| | | | |
|---|---|---|---|
| 5,671,730 A | 9/1997 | Ollila | |
| 5,865,173 A | 2/1999 | Froehlich | |
| 5,892,339 A * | 4/1999 | Park et al. ................ | 318/400.38 |
| 6,321,748 B1 | 11/2001 | O'Mahoney | |
| 6,953,354 B2 * | 10/2005 | Edirisuriya et al. .......... | 439/191 |
| 6,968,842 B1 | 11/2005 | Truschel et al. | |
| 6,982,532 B2 * | 1/2006 | Mullin et al. ............ | 318/400.41 |
| 2002/0017302 A1 | 2/2002 | Fukunaga et al. | |
| 2002/0134378 A1 | 9/2002 | Finnegan et al. | |
| 2004/0226562 A1 | 11/2004 | Bordewick | |
| 2005/0031322 A1 * | 2/2005 | Boyle et al. .................... | 388/800 |
| 2005/0121989 A1 * | 6/2005 | Suzuki ..................... | 310/156.06 |
| 2005/0210622 A1 | 9/2005 | Baecke et al. | |
| 2006/0061224 A1 * | 3/2006 | Mullin et al. ................... | 310/91 |

FOREIGN PATENT DOCUMENTS

| | | |
|---|---|---|
| WO | 9702064 A1 | 1/1997 |
| WO | 97/10019 A1 | 3/1997 |
| WO | 9922794 A1 | 5/1999 |
| WO | 0202169 A1 | 1/2002 |
| WO | 0226305 A2 | 4/2002 |
| WO | 0232489 A1 | 4/2002 |
| WO | 2004112879 A1 | 12/2004 |
| WO | 2005/016217 A2 | 2/2005 |
| WO | 2005097248 A1 | 10/2005 |

* cited by examiner

* Zero crossing fro EMI control

APPARATUS FOR DELIVERY OF PRESSURISED GAS

FIELD OF THE INVENTION

This invention relates to systems, devices and methods for delivering breathable gases. In particular, the invention relates to systems, devices and methods for delivering gases at constant or variable flow rates, pressures, and humidity. More particularly, this invention relates to devices and methods for delivering breathable gases to masks for treatment of breathing disorders.

BACKGROUND

There are a number of devices available for the delivery of breathable gas, including air, to a patient for the treatment of disordered breathing, in particular, sleep disordered breathing. For example, in the treatment of sleep apnea, including obstructive sleep apnea, air is often delivered at continuous positive air pressure (CPAP) wherein air is supplied continuously at a pressure greater than ambient to the airway of a sleeping patient through a mask to keep the patient's airway open for effective respiration.

It is important for continuous therapeutic benefit from pressurised air for the air and other gases to be delivered at a pressure and a flow rate appropriate for the desired breathing pattern. The delivery of gas should not induce the feeling of "blowing into the wind" during treatment. It is known in the art that a system including a gas delivery device, often with gases humidified for comfort, incorporates various combinations of fans, air conduits, face masks, and mask assemblies. Gas-delivery devices may be controlled by circuitry and computer software to deliver the gas through an air conduit to a face mask at a desired flow rate and pressure.

Prior art gas-delivery systems, methods, and devices generally include a limited number of desirable features. For example, gas may be delivered at only one or a limited number of flow rates. Similarly, gas may be delivered simply as pressurised air, the unhumidified pressurised air having the potential to cause discomfort by drying out the breathing passages of a patient using the gas for treatment. A device delivering gases may be large and cumbersome to manipulate. It is known in the art that fans used in devices can be noisy and cause disturbance to the sleep of patients using the devices. Prior art devices are known wherein flow rate is controlled by changes in motor speed. Such devices are limited in efficacy of controlling flow rate by the speed with which pressure change can be effected by the dynamics of the motor.

What is needed is a gas-delivery system and methods for delivering gases that include devices that are relatively easy to manipulate, operate, quiet, and deliver gases with appropriate humidification at desired flow rates and pressures. Further, a gas-delivery system should be relatively easy to manufacture and to transport. A gas-delivery system should be able switch between pressure levels quickly to accommodate expiratory and breath changes.

A reference herein to a gas-delivery system includes systems, and devices for CPAP, VPAP (Variable Positive Air Pressure), BiPAP (Bi-Level Positive Air Pressure), or APAP (Automatic Positive Air Pressure), all of which describe the flow rate and pressure of gases delivered by a device or a system. For example, BiPAP switches to a lower airflow when appropriate during expiration by a patient so that the patient has more comfortable breathing by not having to breathe into a "force of air". Further acronyms used to describe elements in this document are provided with their meanings in Table I. In this document a reference to "comprising" is a reference to "including", where both words are used in a context that is not limiting.

SUMMARY OF THE INVENTION

Figure 1:
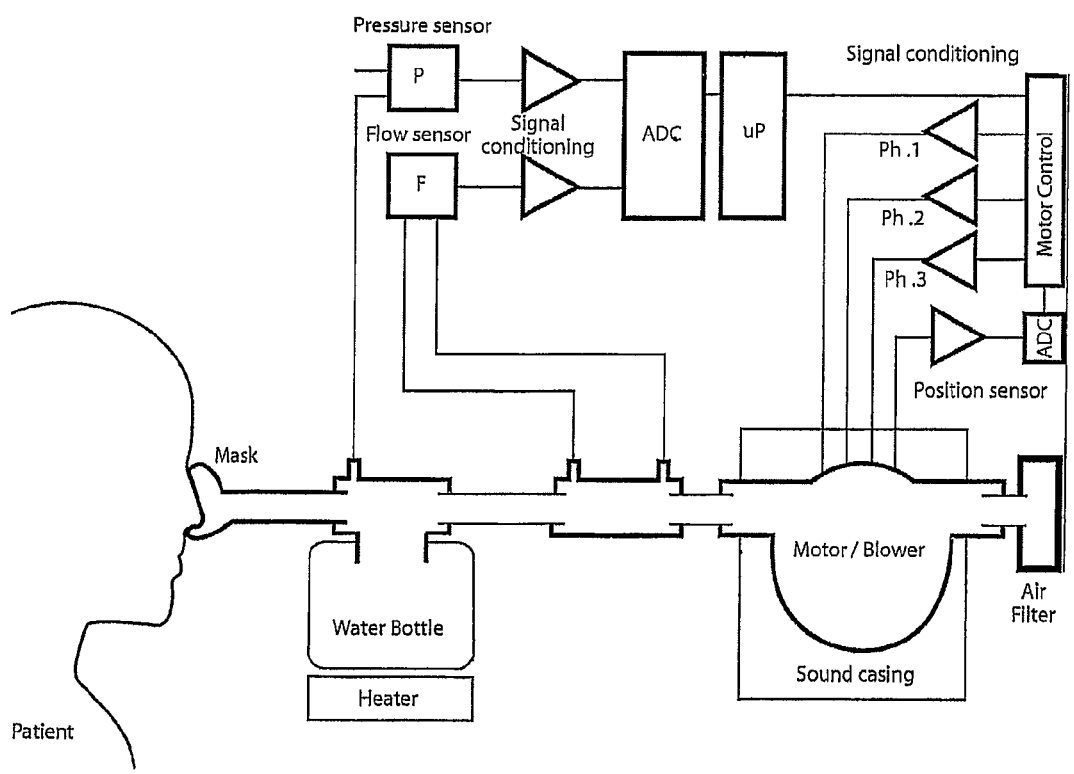
FIG. 1 shows a diagram of a pressurised gas delivery system.

It is an object of the invention to provide a simple humidification system for the pressurised gas. It is a further object of the invention to provide a gas delivery system that is relatively easy to use. It is a further object of the invention to provide a method for delivering humidified gas through a conduit to a subject.

The invention provides a gas-delivery system that incorporates a humidifier assembly including a removable water reservoir. The invention provides that the humidity level of the gas passing over the water may be selected by the device user. The invention advantageously incorporates that the controlling variable in setting the humidity level is by adjustment of the temperature of the water in the reservoir. The water reservoir in a gas-delivery device constructed according to the invention can be easily removed for cleaning or replacement.

The invention may incorporate a pressure-sensing means to detect gas pressure at a location near the location where the conduit for delivering pressurised gas from the gas-delivery device engages the device. This arrangement advantageously allows the pressure of the gas delivered through the conduit to be calculated as a function of variables including the sensed pressure, taking into account the parameters of the mask type and conduit length.

It is a further object of the invention to provide a gas-delivery device and system that incorporate the ability to make rapid changes in gas pressure and flow rates in order to effectively provide gas to the airway of a patient while accommodating patient breathing patterns. The system elements cooperate to reduce pressure fluctuations at the patient mask while the patent is breathing during treatment. The invention provides a gas-delivery system that is controlled by computer software running on a microcontroller. According to the invention, outputs from the measured pressure, flow rate, temperature, and humidity sensors are conveniently converted to digital values for subsequent signal-processing by analogue-to-digital converters (ADCs). The invention provides that a microcontroller sets the desired instantaneous gas pressure in the conduit and face mask by adjusting the motor speed of the fan according to the computer software. The invention provides a method of motor-speed control wherein the signal from a single rotor position sensor is digitally processed to determine the current speed, position and three-phased winding drive signals. The invention incorporates that the motor has a sufficiently small inertia to allow the gas-delivery device to respond rapidly to changes to pre-determined gas-pressure settings.

The humidification system includes water reservoir for humidification of delivered gas, the water reservoir engaging and sealing with the conduit when the device lid is in a closed position. The invention further provides a water reservoir that engages with a heating plate when the device lid is in a closed position. The heating plate biases the water vessel to so engage the heating plate. The invention further provides a water vessel that is integrated with the gas-supply system. The invention provides a port combining an air inlet and outlet port for the water reservoir, which advantageously simplifies the refilling of the water reservoir. The simple construction of the water reservoir, which is preferably comprised of a polymer that can be blow-molded, advantageously reduces the cost of manufacture of the water reservoir. Most advantageously, the water reservoir can be easily cleaned or replaced.

The invention provides a rigid isolation chamber around the blower to effectively muffle sound emanating from the blower. It is preferably made from metal, more preferably a zinc die casting, preferably with walls of the isolation chamber being generally greater that 1.6 mm thick. Integral components in the isolation chamber include one or more plenum chambers that effectively attenuate sound transmission along the air pathway. In addition the entire isolation chamber advantageously behaves as a Helmholtz resonator, the frequency of which can be modified by providing-inlet and/or outlet passages with, preferred dimensions. Preferably the inlet and/or outlet passages are generally circular in cross-section and of a sufficient length to minimise the resonant frequency of the isolation chamber without causing excessive flow restriction.

The invention provides that the configuration of the components of a gas delivery device allow the gas delivery device be disposed in alternative mounting orientations, in any suitable orientation from horizontal or vertical. The invention provides most advantageously for an embodiment including a vertical disposition of the gas-delivery device, which enables wall mounting of the device.

The invention provides most advantageously that the gas delivery device includes an air filter that may be housed in a removable transparent casing, the dirty side of the filter being visible through the transparent casing.

The invention further provides a graphical user interface (GUI), which facilitates configuration of the device, setup and patient history feedback. According to the invention, the GUI may include an alarm clock function.

The invention provides that device patient-specific configuration, and sleep study data may be recorded on removable SD Card media. This feature provides flexibility in invention setup and subsequent data analysis by a laboratory remote from the invention as the patient need only transport the SD Card.

In one aspect, the invention provides apparatus for delivering breathable gas to a subject, comprising a blower for delivering pressurised gas a water reservoir for humidifying the gas, a heater, a casing for housing the blower and the water reservoir, a gas inlet and a gas outlet each engaging a single port in the water reservoir, and a conduit for directing gas from the outlet to a subject.

In another aspect the invention provides apparatus for delivering breathable gas to a subject, comprising a blower for delivering pressurised gas, the blower disposed in a sound housing, a casing for housing the blower and a water reservoir, a heater for heating water in the water reservoir, a gas inlet and a gas outlet, a gas filter housed in a removable transparent casing, and a conduit for directing gas from the outlet to a subject.

In a further aspect, the invention provides apparatus for delivering breathable gas to a subject, comprising: a blower for delivering pressurised gas, a casing for housing the blower, a heater, a gas inlet and a gas, outlet, a conduit for directing gas from the outlet to a subject, and at least one plenum chamber and at least one resonating means adjacent the blower. In this aspect the apparatus may include a water reservoir and a heater for heating the water in the water reservoir.

In a further aspect, the invention provides apparatus for delivering breathable gas to a subject comprising a blower for delivering pressurised gas, a water reservoir for humidifying the gas, a heater, a casing for housing the blower and the water reservoir, a gas inlet and a gas outlet, and a conduit for directing gas from the outlet to a subject wherein the apparatus is disposable in operation at any suitable angle from substantially horizontal to substantially upright orientations without spillage of fluid from the water reservoir.

In a further aspect, the invention provides apparatus for delivering breathable gas to a subject comprising a blower having an outlet for delivering pressurised gas, the blower comprising of a motor chamber, two outlet airways and a valve chamber, the blower including means to rapidly change gas pressure or flow rate; a casing for housing the blower and the water reservoir; a gas inlet and a gas outlet; a gas filter housed in a removable transparent casing, and a conduit for directing gas from the outlet to a subject.

In each of the foregoing aspects, the conduit may be comprised of concentric conduits for inlet and outlet gases. Preferably the inner conduit provides inlet gas.

Preferably the means to change the gas pressure or flow rate is at least one impeller. Preferably, the apparatus includes a time signaling means for a user to determine the time from the apparatus. Preferably the signaling means is a time clock.

In a still further aspect; the invention provides a method for controlling a motor of a blower in a gas delivery device, the method including the steps of determining the rotational position of an impeller determining the velocity of an impeller; and adjusting the timing of winding excitations for controlling the speed of the impeller.

In a still further aspect, the invention provides a method for delivering breathable gas to a subject, the method including the steps of pressurising ambient gas with an impeller, humidifying the ambient gas directing the humidified gas to the airway of a subject wherein the pressurising step includes detecting the position of the impeller with a single sensor means. Preferably the sensor means used in the method is a Hall effect sensor.

DETAILED DESCRIPTION OF THE FIGURES AND MOST PREFERRED EMBODIMENT

The invention is most easily understood with reference to the accompanying figures. It will be understood that the figures are intended to be illustrative embodiments of the invention and that the scope of the invention as defined in the claims includes further embodiments not so illustrated. A diagram of representative elements of a pressurised gas-delivery system is shown in FIG. 1. The invention includes that gas is drawn into a gas-delivery device through a replaceable filter system by a motor and blower assembly, the assembly being, encased in a noise-dampening housing to provide quieter operation of the system. A flow-sensing device, located in series with the gas path, may be used to detect the gas flow. Further aspects within the scope of the invention are included in the following description.

Outer Casing

The following elements are more clearly understood with reference to FIGS. 8 to 14. The outer casing of the gas-delivery device including an upper case 1, a lower case 2, a first side panel 3, a second side panel opposite said first side panel (not shown), and a lid 4. The upper and lower casings can be engaged with suitable engagement means. Preferably, the engagement means are screws. Engagement of the upper and lower casings positions the first and second side panels to form a relatively leak-proof enclosure. In engaged, position, the outer casing is relatively resistant to ingress of water that may be poured on the top of the gas-delivery device irrespective of the orientation of the casing. The lid engages the upper casing with a lid engagement means. The lid engagement means is preferably a snap-fit at the pivot point means. The pivot point means may be any suitable pivoting means such as hinges or hinge pins. Alternatively, and most advantageously, the pivoting means may be a mechanism that includes that the instantaneous point of rotation is not fixed relative to the casing. An example of such a mechanism includes, but is not limited to, a four-bar linkage mechanism. When engaged in a closed position, the lid may be locked in position by a lid locking mechanism 5. The lid locking mechanism is preferably a latch. The latch is preferably spring actuated. Preferably the lid is also spring-actuated to enable it to open when the lid latch is disengaged. If spring actuated, the spring actuating the lid preferably incorporates a rotary damper to create a smooth opening action for the lid and to avoid a "jerky" spring action that might otherwise occur. The pivot point can be located at the top of the casing or it can be located at the back of the casing.

The invention includes that located-on the upper case is a user interface (UI). The UI is preferably constructed from a transparent lens 6 a sealing means between the upper case and the lens, and a flexible keypad 7. The sealing means is preferably a gasket. The keypad preferably includes at least one button. The lens engages with the upper case with a suitable engagement means. Preferably, the lens engagement means is a snap-fit located on each side of the lens. Alternatively, the lens engagement means may be adhesive tape. The lens most advantageously allows the user of the gas delivery device to see through the outer case to a display which communicates information to the user. A further advantage of the lens is that it engages the flexible button keypad in fixed position. A further advantage of the engagement of the lens is a seal which prevents water ingress through the screen or button holes into the upper case. The flexible button keypad is preferably constructed from silicon to allow the gas-delivery device user to advantageously communicate commands to the gas-delivery device.

Air Filter

Figure 11:
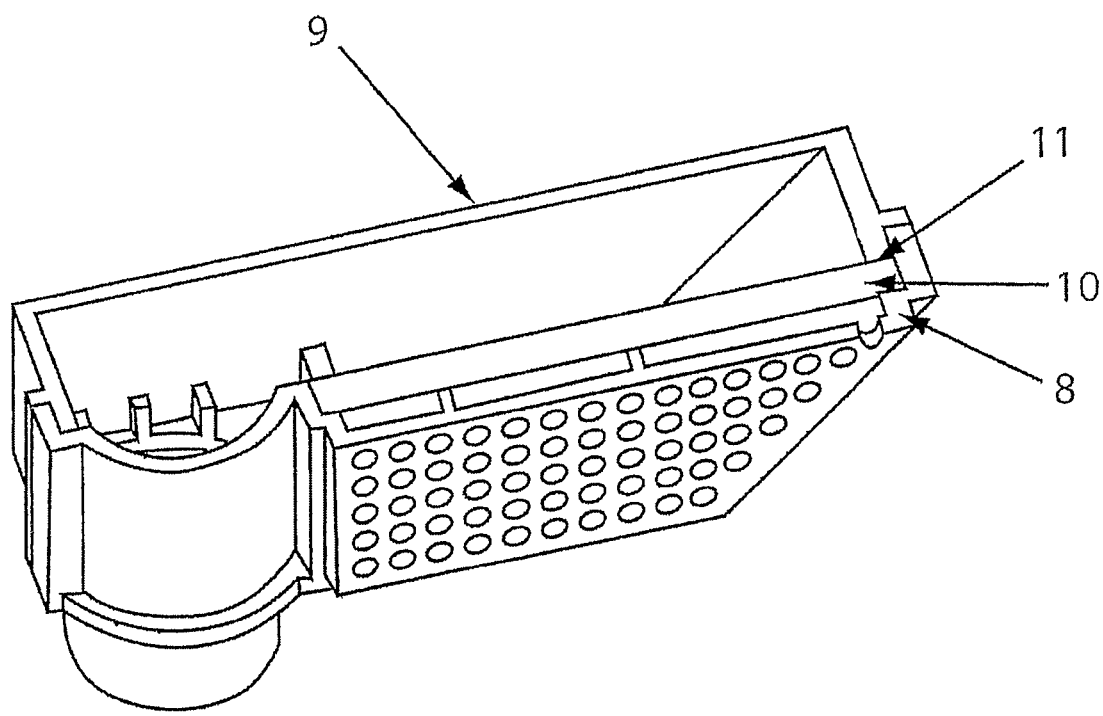
FIG. 11 shows a gas filter in perspective view.

The invention includes that the air filter is comprised of a front case 8, a back case 9 and at least a primary filter 10, illustrated in FIG. 11. Preferably the casing material is transparent. Preferably the air filter incorporates a secondary filter 11. The invention includes that the front case engages the back case to create a channel including the at least primary filter and preferably the secondary filter. Preferably the engagement means comprises of snap-fits. In operation of the gas-delivery device the engagement of the front case and base case creating the channel requires that gas delivered by the gas-delivery device must pass through the filter media. The filter media may include a primary and a secondary medium. The filter front case includes a plurality of holes to allow gas to flow into the primary filter and to contact the surface of the primary filter media to achieve filtering. Preferably, the cross sectional area of the holes is greater than 400 mm$^2$ to avoid restricting flow into the primary filter. The filter back case includes an aperture which receives a connector attachment of the upper case, which in turn, provides a good seal when engaged. Preferably the connector attachment is a male tube. The filter engages with the upper casing under the lid. Most advantageously, the operation of the filter casing allows for removal and replacement of the filter. Replacement of the filter will ensure ongoing filtration of the intake air for the use of the gas-delivery device constructed according to the invention.

The primary filter media enables the removal of large dust particles from the gas, while the secondary filter media is intended to remove smaller particles. The invention includes the use of a range of secondary filter media. Examples of media include media suitable to remove; pollen, bacteria, smoke and smog air pollution and viruses. It will be understood that the range of filter media is not limited by the preceding list.

Blower/Motor

The invention includes that the blower may be comprised of elements in different configurations as exemplified herein. It will be understood that other configurations are within the scope of the invention as claimed.

Figure 9:
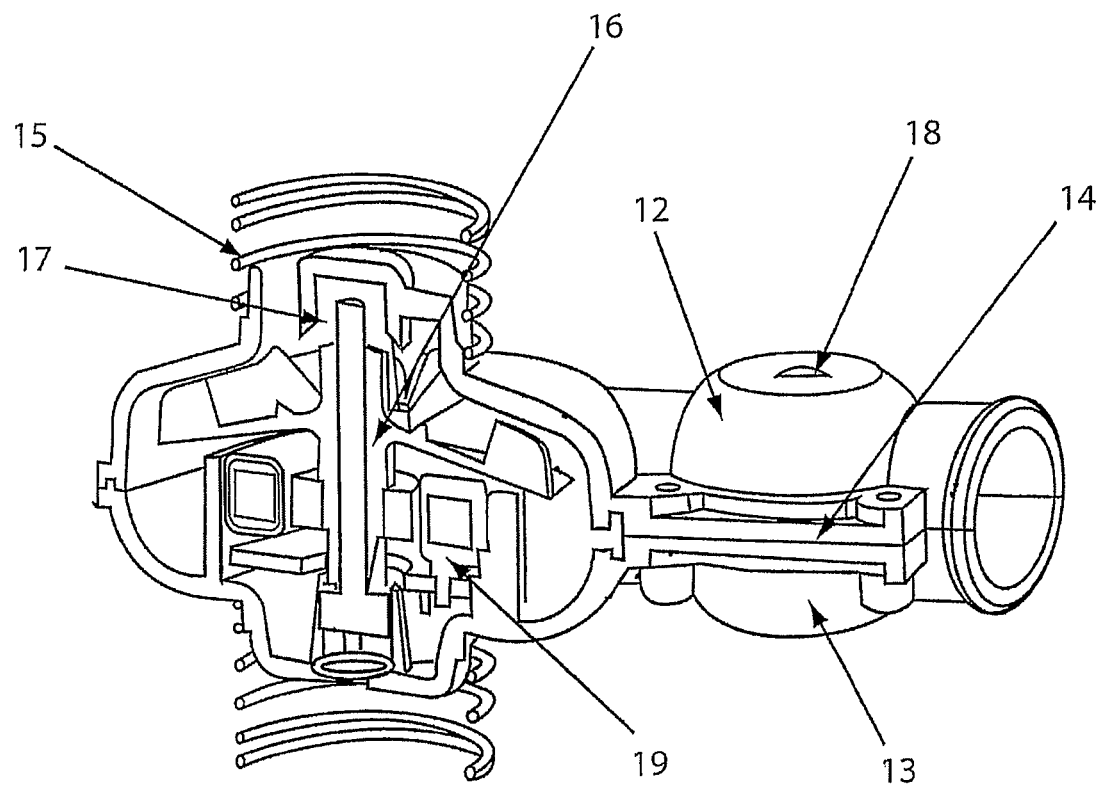
FIG. 9 shows a side view of a blower with a portion in cross section.

In a first embodiment of the invention as shown in FIG. 9, the blower is constructed from a top casing 12 a bottom casing 13 and a dividing septum plate 14. These elements are engaged using screws or other engagement means to seal airtight and create a blower chamber, a motor chamber, two outlet airways and a valve chamber. The blower chamber houses the impeller 16 which is mounted on a shaft with bearings at each end 17. Preferably one bearing is press-fit into the top casing and the other is located, in the bottom casing to enable it to move axially within the casing. Preferably, a helical spring conveniently maintains an effective axial pre-load on both bearings. Preferably, the bearings are lubricated with low-noise grease. The impeller 16 may have a series of fins on its top surface to move air as the impeller rotates. The invention includes that between each of the fins is a small gap between the top and bottom surfaces of the impeller. In combination, the features allow the majority of the air flow generated by the impeller to flow out of the blower chamber into the top outlet airway (formed by the top case and the septum plate) and to create a higher pressure in this airway. The small holes also allow some air to flow into the bottom outlet airway (formed by the bottom case and the septum plate) and to create a reduced pressure in this airway. Within the valve, chamber a valve member 18 then regulates the amount of air passing out of each of the top outlet airway and the bottom outlet airway. This valve 18 most advantageously can change the pressure of the overall outlet air very rapidly without the motor needing to change the speed of the impeller. The motor chamber contains the motor mechanism and electronics, which are held firmly in position by the bottom casing 13 and the septum plate 14.

Figure 10:
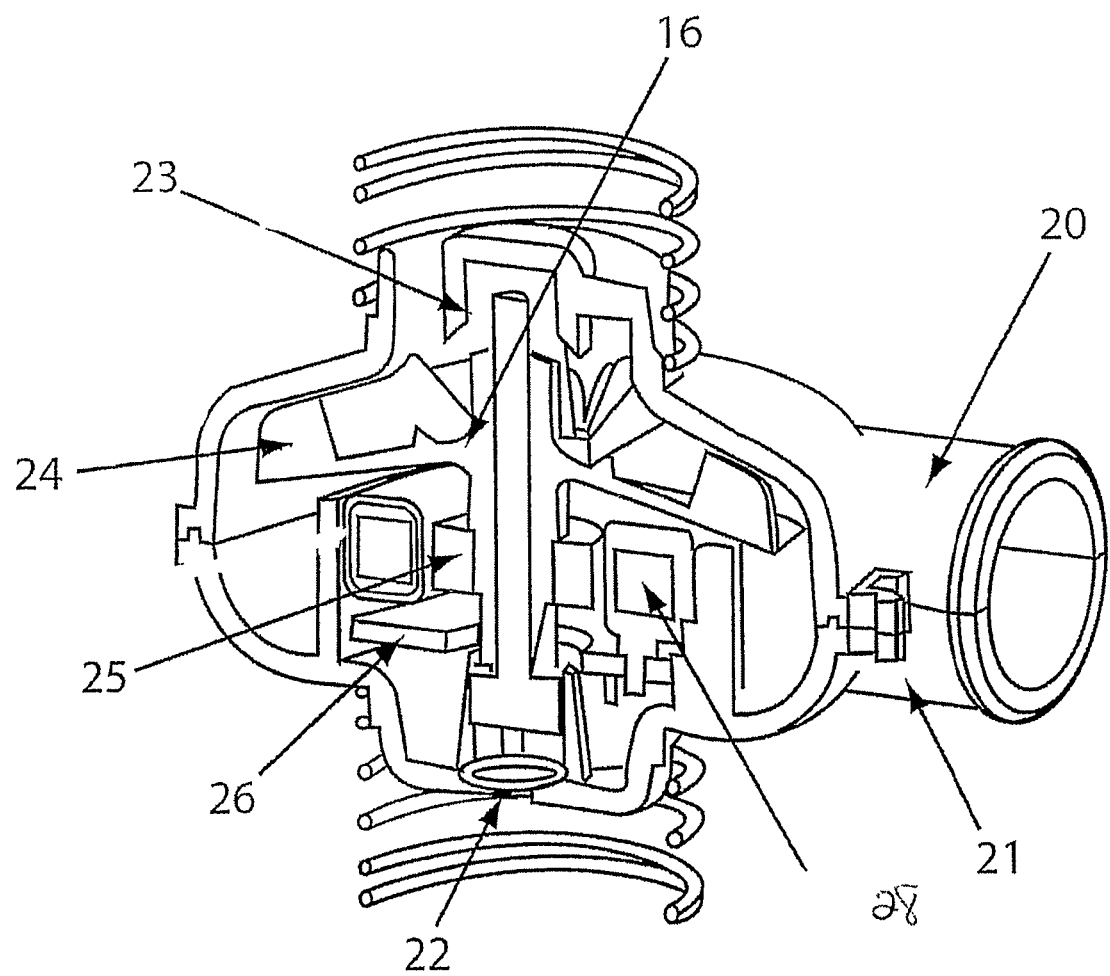
FIG. 10 shows a side view of a blower with a portion in cross section.

In a second embodiment of the invention, shown in FIG. 10, the blower includes a top case 20 and a bottom case 21 which engage to form an air-tight seal with suitable engagement means. Preferably the engagement means includes screws. The engaged cases form a blower chamber, a motor chamber, and an outlet path. Within the blower chamber is located the impeller 16 which has two bearing sets 23 mounted to either end of the blower chamber and a magnet mounted 25 to the middle of central shaft of the chamber. The top bearing set 23 is pressed into the top case and the bottom bearing is held radially in the bottom case and vertically by an impeller spring 22. Preferably, the impeller 16 and shaft are moulded in one piece from a glass-filled polymer. Alternatively they may be over-moulded as a polymer onto a metal shaft.

The top housing includes a gas inlet located above the blower chamber which allows gas into the blower chamber. The impeller has a series of fins 24 located on its top surface designed to move the air to the outlet as the impeller rotates. This movement of gas creates an increase in pressure at the outlet which can be regulated by the speed of the impeller rotation. The bottom surface of the impeller is located in close proximity to a wall on the bottom casing which advantageously forms the motor chamber. Within the motor chamber the motor windings 19 and electronics 28 are firmly located in position by snap-fit or other suitable means and provide the power which drives the impeller rotation.

Preferably the motor uses a toroidal core with no magnetic cogging. Three phase windings are used in star configuration, supplied with sinusoidally-modulated power (SPWM) to minimise torsional excitation. Preferably, the rotor is comprised entirely of precision moulded plastic, which most advantageously avoids the need for an internal metal shaft and dynamic balancing. The invention includes that electronic commutation is phased from a single Hall Effect sensor mounted adjacent to the rotor magnet.

Sound Housing

Figure 13:
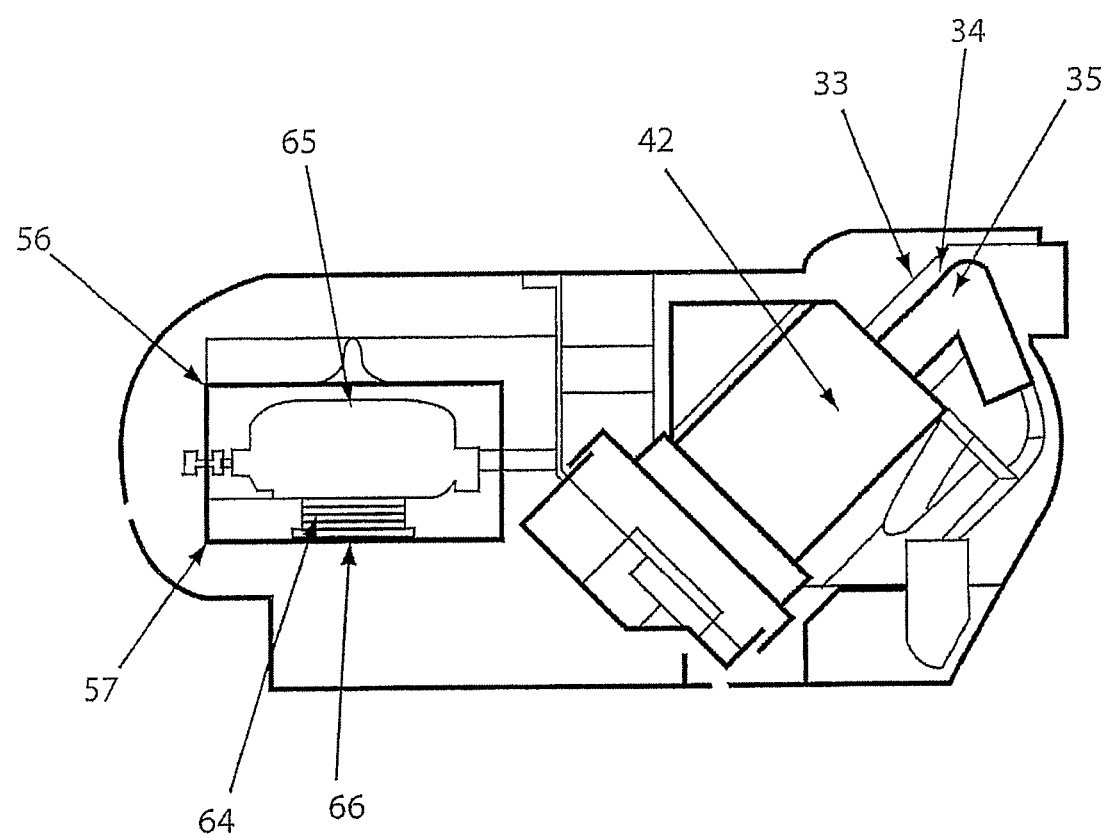
FIG. 13 shows show a side view in longitudinal section of a gas delivery device.
Figure 14:
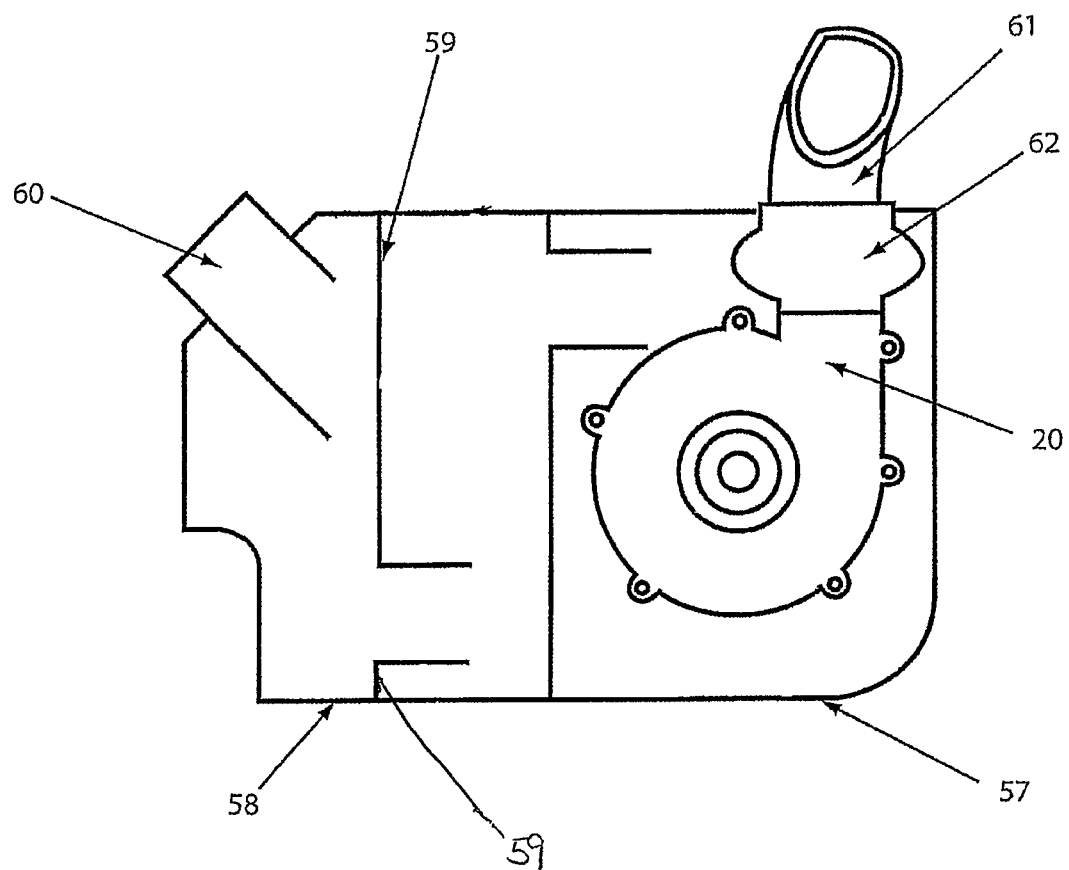
FIG. 14 shows a top view of a blower inside a sound housing for a gas delivery device.

The invention includes that in one embodiment, as shown in FIGS. 13 and 14, the sound housing is constructed from an upper housing 56, a lower housing 57 a sealing gasket 58, two divider walls 59, inlet pipe 60, outlet pipe 61, a flexible blower attachment 62 and the blower as herein described. The upper and lower housings preferably are moulded or cast from a dense material to reduce sound transmission from the inside to the outside of the casing therefore contain the sound within. Preferably, the dense material is zinc or a mineral-filled plastic. The upper and lower housings engage with engagement means to position the two dividing walls, the inlet tube and the outlet tube, compressing a sealing gasket around the periphery to seal air tight. Preferably, the engagement means are screws. This engagement of the housings according to the invention creates three chambers, the blower chamber, a primary sound chamber and a secondary sound chamber. Within the blower chamber is located the blower 20. Preferably the blower is mounted on two springs, first 64 and second 65, which ensures the blower has a low resonant frequency. The springs operate to reduce the transfer of vibration from the blower to the sound housing. Preferably, to increase the noise isolation effect, a flexible pad 66 is located between the second spring and below the housing. At the blower outlet a flexible tube fixes the outlet to the outlet pipe 61. Preferably the flexible tube has corrugated sides. In this embodiment the flexible tube forms part of the sealing gasket 58. Preferably the flexible tube is moulded from a TPE material. Alternatively, it may be a separate part. The dividing walls 59 separate the chambers and reduce the sound transfer from one chamber to the next. Preferably, the dividing walls may include a tube, the tube extending into the next chamber. The function of the tube is to carry all of the air flow between the chambers. Preferably, the tube is located with its end a small distance, sufficient to not restrict the airflow, from the opposing wall of the next chamber. Preferably the opposing wall is covered in a sound deadening foam or other suitable material to inhibit the sound transmission into the tube and therefore between the chambers.

Humidifier

Figure 12A:
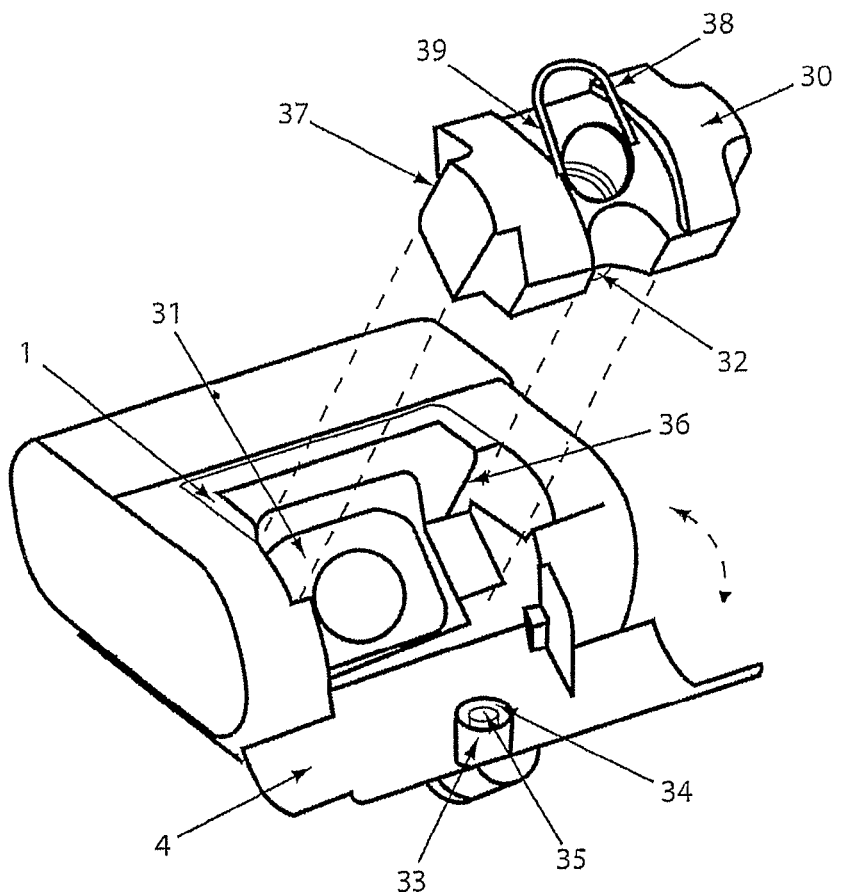
FIG. 12a shows a top perspective view of a gas delivery device with water reservoir positioned outside the gas delivery device.
Figure 12B:
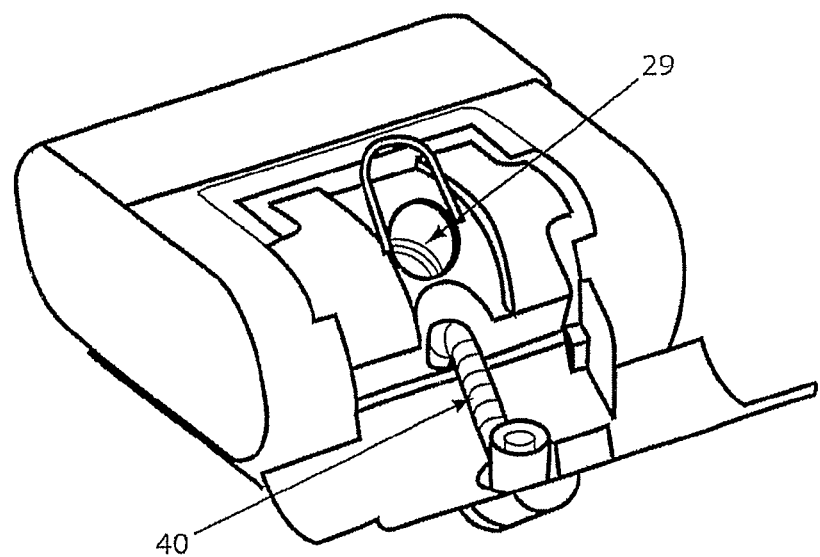
FIG. 12b shows a top perspective view of a gas delivery device with water reservoir operatively positioned inside the gas delivery device.

The present invention includes a humidifier that is incorporated into the gas-delivery device enabling the gas delivery and humidifying functions to cooperate in operation of the device. As shown in FIG. 12, the humidifier includes a water reservoir 30, a gas conduit connector 33, an air seal 28, a set of heating plates 31 with internal ceramic heater, and a water-reservoir heat-conductor 32. In operation, the humidifier is concealed under the lid 4.

The water reservoir 30 is preferably comprised of a blow-moulded thermoplastic. The water reservoir surface includes portions that are straight and flat, the portions corresponding to receiving surfaces or rails 36 on the upper case 1. In operation, the rails ensure the water reservoir is placed correctly in the apparatus and held firmly in place. In a preferred embodiment of the invention, the water reservoir cannot be inserted into the apparatus in any other than the correct position. In position the water-reservoir heat-conductor 32 engages the upper heating plate 31 by the operation of a biasing means 37 that biases the heating plate toward the water reservoir, ensuring efficient heat transfer between the heater and the water. The biasing means 37 is preferably a heating plate spring. Most advantageously, the invention includes that the metal lid may be of the type commonly found in food packaging. The invention includes that a handle 38 may extend from the water reservoir. In such an embodiment the handle preferably includes at least one integrated hinge 39. Preferably the integrated hinge is moulded flat so that the handle automatically pops up for convenient finger access when the lid 4 is disengaged into the open position. The handle 38 is also convenient for carrying the water reservoir from the apparatus to a household water tap.

In operation the water reservoir 30 is filled with water and replaced in position in the apparatus, allowing engagement of the lid 4 into a closed position. The gas conduit connector 33 nests into the lid 4 to move and hinge as one component. Once the lid 4 is engaged, the outer surface of the gas conduit connector 33 is also positioned to simultaneously engage with the water reservoir air seal 28 at the water reservoir opening 29. In operation disengagement of the lid 4 also disengages the gas conduit connector 33 simultaneously from the water reservoir to enable fast and easy access and removal of the water reservoir 30.

Preferably the gas conduit connector 33 is attached to a flexible gas conduit 40 providing pressurised gas into the gas inlet 35 and maintaining an air seal at both ends of said flexible gas conduit while the lid 4 is in the open or closed positions.

A most advantageous aspect of the invention is the single aperture 29 for both the gas inflow and outflow from the gas-delivery device. The invention includes that a gas conduit connector 33 incorporates adjacent gas inflow conduit 35 and gas outflow conduit 34. Preferably, the gas flow conduits are concentric tubes. Preferably, the gas inflow conduit 35 is located inside the gas outflow conduit 34. In operation, pressurised, dry gas moves from the gas inflow conduit 34 to the water reservoir 30 to make contact with the warm water surface 42 where the gas becomes humidified before flowing through the gas outflow conduit 34.

The invention includes a compact water reservoir large enough to hold adequate water to humidify enough breathing gas for a patient for a long night of sleep. The water reservoir is constructed so that a surface engages with the heating surface of the heater, which is disposed generally at an acute angle of approximately 45 degrees. The location of the aperture 29 on a surface that is generally parallel with the surface engaging the heating surface allows the gas-delivery device to be disposed can lay in a horizontal orientation, such as on a bedside table, or in a vertical orientation, such as on a wall, or any convenient intermediate orientation, without compromising the operation of the apparatus and its humidifier. Most advantageously, changing the angle of the apparatus by 20 degrees in any direction off the horizontal or vertical orientation will not result in any leakage of water from the water reservoir 30.

Figure 6:
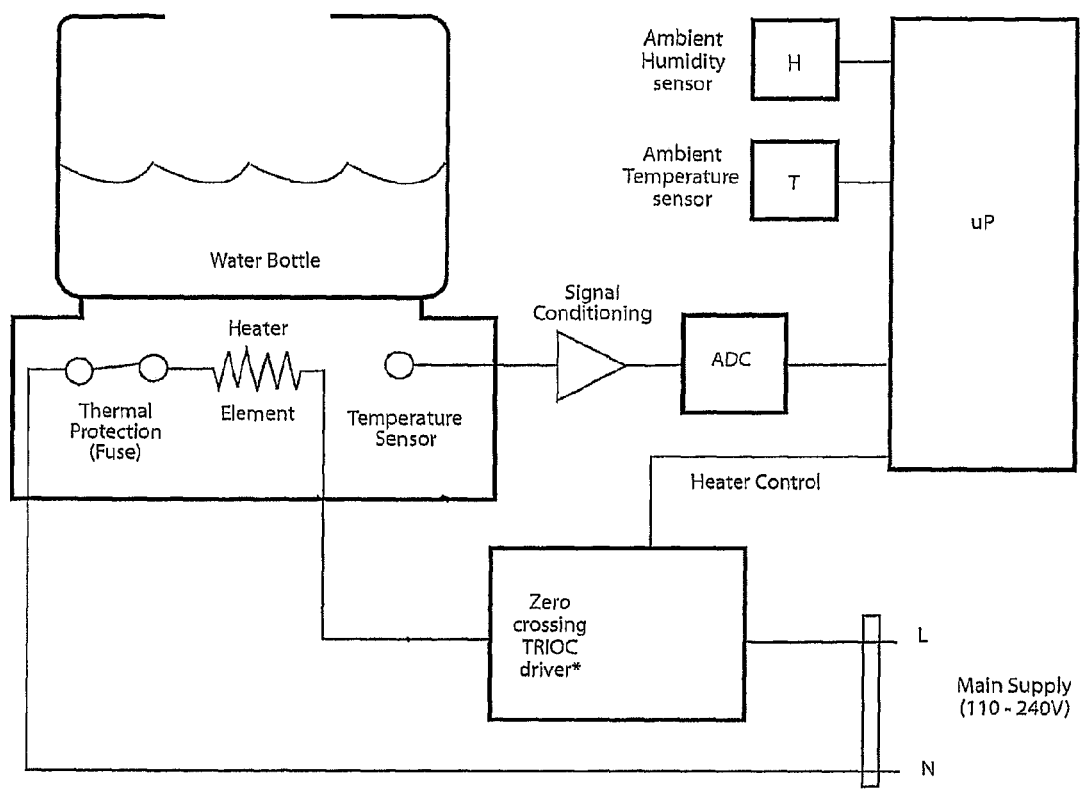
FIG. 6 shows the humidifier components of a gas delivery device.

FIG. 6 is a schematic diagram showing the operation of a humidifier constructed according to the invention. The temperature of the heater plate is the sole controlled variable in setting the gas humidity. The duty cycle of the heating element is used to control the heater plate temperature. A photo-coupled zero-crossing trlac driver is used to turn a trlac on and off under control of the micro controller. The photon-coupling includes the isolation from the trlac driver output (at mains potential) and the micro-processor control signal. Zero-crossing switching reduces the EMI produced by the trlac.

The invention includes that a computer program running on the microcontroller controls the heater plate temperature to produce a user-selected humidity level. In one embodiment the gas-delivery device includes an ambient air temperature sensor and a plurality of user-requested humidity levels. The invention includes that the temperature of the air and the heater plate inputs, plus the air flow-rate, can be used by the computer program to set the heater plate temperature. Preferably, the gas-delivery device includes a humidity sensor for ambient air to allow more, precise control of humidity.

The invention includes that the humidifier is comprised of a mains-powered heater switched preferably by a trlac, a thermostat attached to the heater plate, and a thermistor attached to the heating plate to provide the software with temperature feedback. An ambient air temperature sensor to help determine the water temperature for the user selected humidity, and a humidity sensor which may be mounted near the case extremity and shielded from heat sources inside the case.

The gas-delivery device may include a manual reset button for the heater plate thermostat, which need not be accessible by the user, to provide over-temperature protection in the event of a fault condition.

Motor Control

Figure 2:
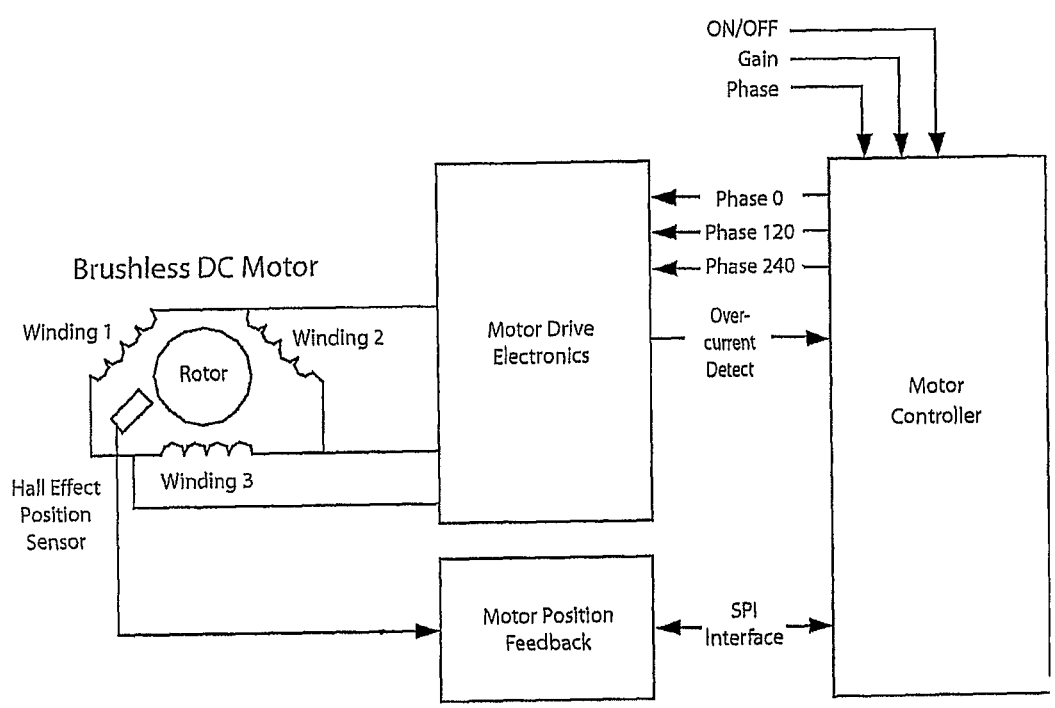
FIG. 2 shows a diagram of a motor controller for a gas delivery device.

The control of the motor of the blower enables the blower to make rapid changes in gas pressure and flow rate. As shown in FIG. 2, the gas-delivery device includes a motor and motor controller for a gas-delivery device, the motor and motor controller comprised of the major subsystems:
- brushless DC motor incorporating a single Hall Effect sensor for rotor position sensing
- Digital Motor Controller,
- motor driver and over current detection electronics, and
- Hall Effect sensor signal conditioning and analogue-to-digital converter (ADC).

Brushless DC Motor

Brushless DC Motors known in the art require three Hall Effect sensors to provide the required rotor position information. The present invention incorporates a method of control that requires only a single Hall Effect position sensor.

The gas-delivery device includes a motor that includes three windings, the windings configured in a star topology. According to the invention, the windings are energised in a predefined sinusoidal sequence in order to initiate and maintain motor rotation. The duty cycle of this sequence determines how much power the motor consumes, which in turn, governs the motor speed.

Motor Drive Electronics

The motor drive subsystem includes the electronics necessary to power the motor windings and sense the motor current. The motor drive includes six MOSFETs arranged in a configuration of three half-bridge drivers. These FETs provide power to the motor windings, it also contains the necessary level translators to convert LVCMOS signals from the Motor Controller into the appropriate MOSFET drive signals.

Figure 3:
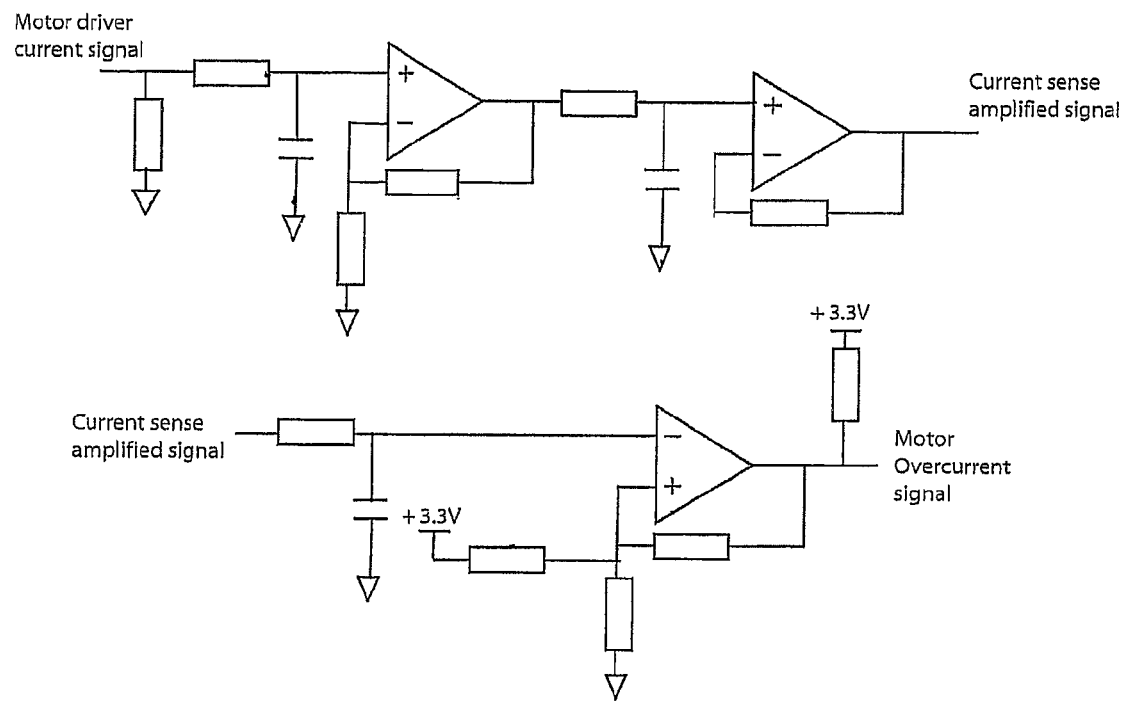
FIG. 3 shows a motor current sense circuitry.

Motor-current sensing-circuitry, illustrated in FIG. 3, is used to signal an over-current condition to the motor controller. This allows the controller to shut down the motor in the event of an over-current fault. According to the invention this is implemented by a fixed-level over-current threshold detector. The invention includes two parts to the current feedback subsystem. A first part is a simple low-pass filter amplifier to amplify and filter the voltage over the current sense resistor. A second part is a simple comparator with hysteresis to detect an over-current fault. The output of the comparator drives directly into the motor controller.

Motor Position Feedback

According to the invention the motor has a single Hall Effect sensor that is used to detect the position of the rotor. The signal is converted to a digital value by an ADC.

Motor Controller

According to the invention, the motor controller spins the gas-delivery device motor. According to the application, eg. CPAP, APAP, BiPAP, or VPAP, the controller causes the motor to spin at an appropriate frequency. It uses a single Hall Effect sensor to receive rotor position feedback and it uses this to generate three sinusoidal PWM drive signals.

The motor controller includes the following inputs and outputs:
- ON/OFF. Input to turn motor on or off via the microprocessor interface.
- Motor Gain. Input to set motor speed via the microprocessor interface.
- Phase. Input to set the relative phase between the Hall Effect position sensor and Phase 0 drive to motor winding 1.
- Over-current. This input signals an over current condition has occurred and causes the Motor Controller to stop the motor.
- SPI Interface. The bidirectional SPI interface periodically samples the Hall Effect position ADC and transfers the data into the controller.
- Phase 0. High and Low signals for motor winding 1 drive electronics.
- Phase 120. High and Low signals for motor winding 2 drive electronics. This signal is 120 degrees out of phase with respect to Phase 0.
- Phase 240. High and Low signals for motor winding 3 drive electronics. This signal is 120 degrees out of phase with respect to Phase 120.

Figure 4:
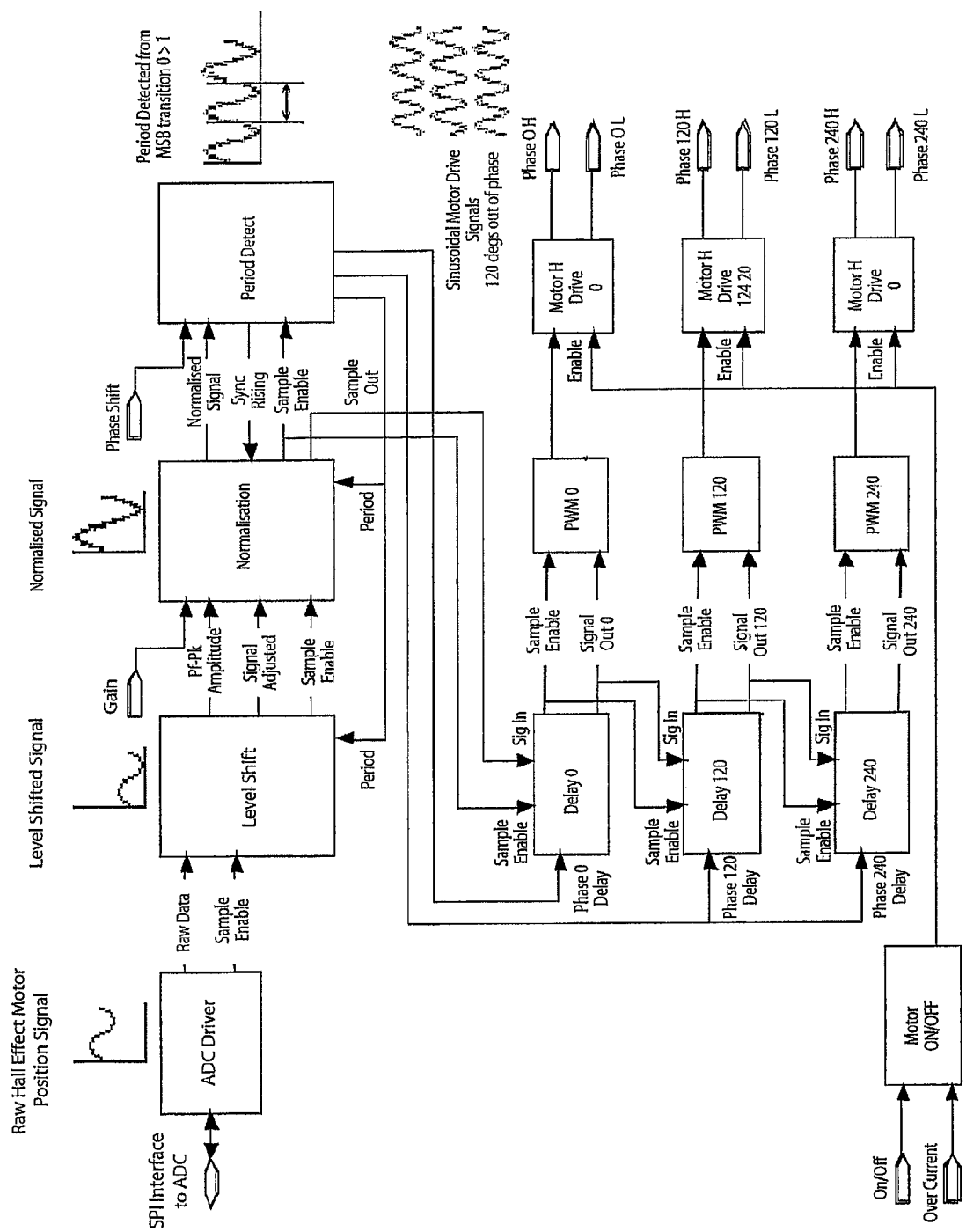
FIG. 4 shows a block diagram of a motor controller.

The motor controller block diagram shown in FIG. 4 is herein described as an illustration of implementation of the invention.

ADC Driver

The ADC Driver is an SPI interface that samples the Hall Effect Sensor ADC every 2040 clock cycles (5.1 μs). It outputs the raw rotor position as a 12-bit number and generates a sample enable signal with each new sample. This triggers the following subsystems to process the new data. When rotating, the output of the Hall Effect sensor is a sinusoid when represented graphically. The graphic above the ADC Driver block in FIG. 4 shows the digitised raw Hall Effect Sensor signal obtained for 1 rotor revolution. The 'y' axis represents the ADC value (0 to 1023). Note that the minimum value is always >0 and the maximum is always <1023.

Level Shift

The rotor position is processed to work out the period and maximum and minimum values. This subsystem calculates the peak to peak amplitude (max ADC value−min ADC value) of the position-sensor raw data samples. This value is recalculated every eight motor periods. The current raw data sample is level shifted by subtracting min ADC value from it and output to the Normalisation subsystem as Signal Adjusted. FIG. 4 shows the Level Shifted waveform.

Normalisation

This subsystem processes the peak to peak amplitude and current Signal Adjusted sample to normalise the signal so that the position is within the range of 0 to 1023. FIG. 4 shows the Normalised waveform. The normalised signal is clipped to 10 bits resolution and fed to the Period subsystem where it is processed to determine rotor period. Rotor period is a measure of system clocks per rotor revolution. The motor is commutated by a 12 sample digital sine wave oscillator which is generated from within this subsystem. The sync rising input, signals that the rotor is at the zero crossing position, resetting the sine wave oscillator to position 0. Thus the sine wave oscillator is phase locked to the zero crossing point. After every Period/12 system clocks the current sine wave oscillator value is incremented according to the invention. If motor speed exceeds a predefined level the current sine wave oscillator value is multiplied by the gain input and subsequently clipped to 10 bits. The gain input is a 10 bit value controlled by the microprocessor interface that includes motor speed control. According to the invention, if the motor speed is less than the predefined level the system gain is set to a fixed value in order to ensure reliable motor starting.

Period Detect

The Period Detect subsystem calculates the rotor period in terms of system clocks per rotor revolution. A low-to-high most-significant-bit (msb) transition of the normalised signal input represents the zero crossing point. The number of system clocks between such transitions is given as the period. To provide a level of filtering the period value is an average of current and previous period calculations. The phase input allows a user selectable (via the microprocessor interface) phase shift to be added into the system. This is used to optimise motor performance and accounts for sensor position with respect to winding 1. This is an 8-bit value where a value of 128 represents a phase shift of 180 degrees. The phase 0 delay output contains the number of ADC samples to delay in order to obtain the required phase shift. The phase 120 delay output contains the number of ADC samples to wait in order to obtain a 120 degree phase shift.

Three Phase Generation

The drive signal is passed through 3 delay lines to generate the 0°, 120° and 240° drive signals. The 0° delay line is used to synchronise the zero crossing point to the rotor position. The 120° and 240° delay lines are adjusted dynamically using a third of the period to work out how much each line should be delayed.

Symmetrical PWM Generation

Figure 5:
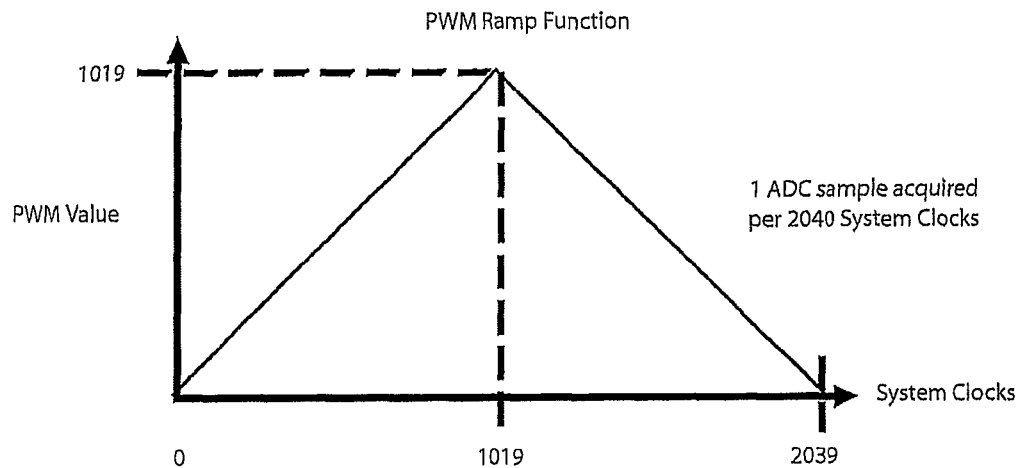
FIG. 5 shows the operation of the motor controller PWM.
Figure 5:
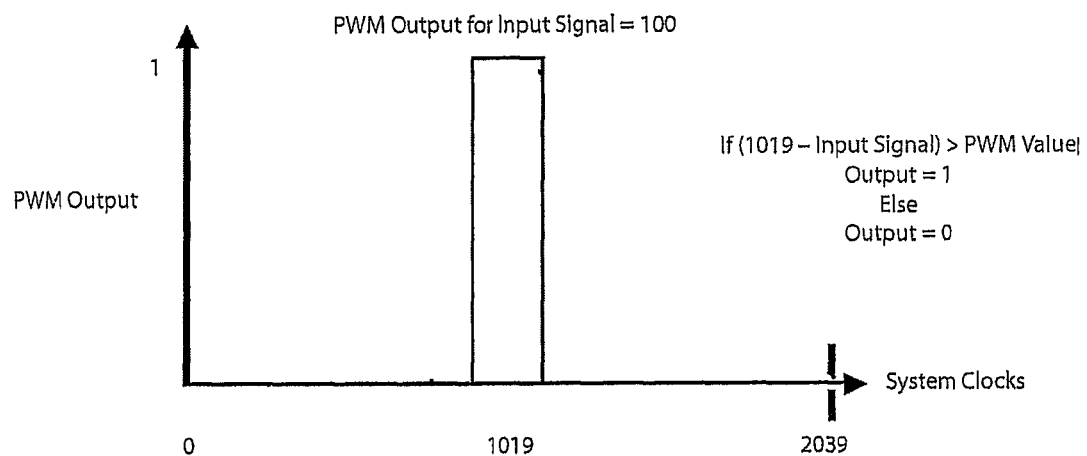
Figure 5:
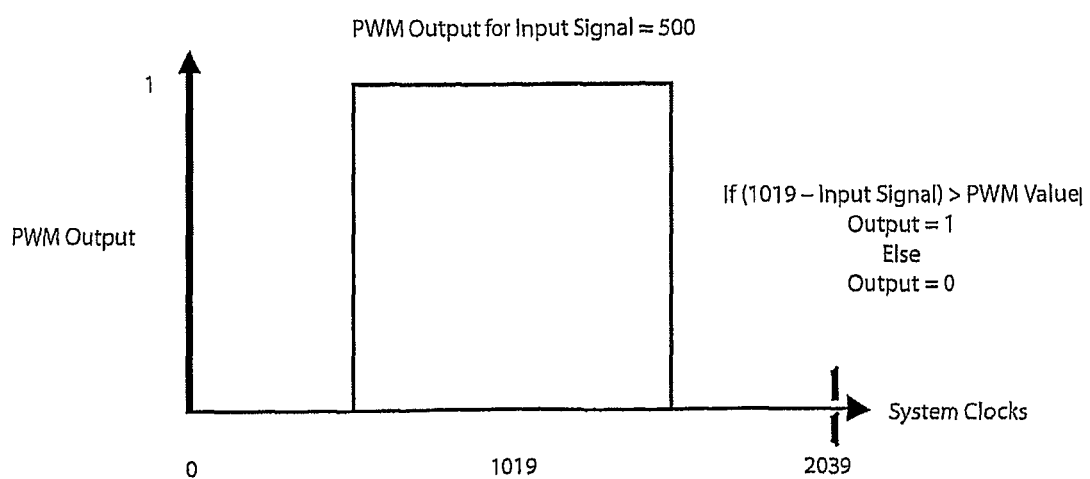

The three sine waves are then pulse-width modulated. The pulses are aligned symmetrically about a centre point. According to the invention this is done by using a triangular reference waveform, rather than the standard sawtooth reference. FIG. 5 shows the operation of the PWM function. Each input sample is modulated by the ramp function, producing a binary output whose logic one pulse width is proportional to the magnitude of the 10 bit input sample. Thus the gain setting in the Normalisation subsystem has the effect of adjusting the duty cycle of the PWM outputs. The larger the pulse width the more power is delivered to the motor and hence the faster the motor will rotate.

Motor H Drive

Each PWM signal is converted into 2 complementary drive signals, one for a N channel FET and the other for a P channel FET. When switching from the N to P FETs (and vice versa) a small amount of dead-time is inserted to prevent both the N and P channels turning on at the same time and shorting the 9V rails. This reduces the power dissipation in the FETs and also noise generation.

Electronic Sub-Systems

Figure 7:
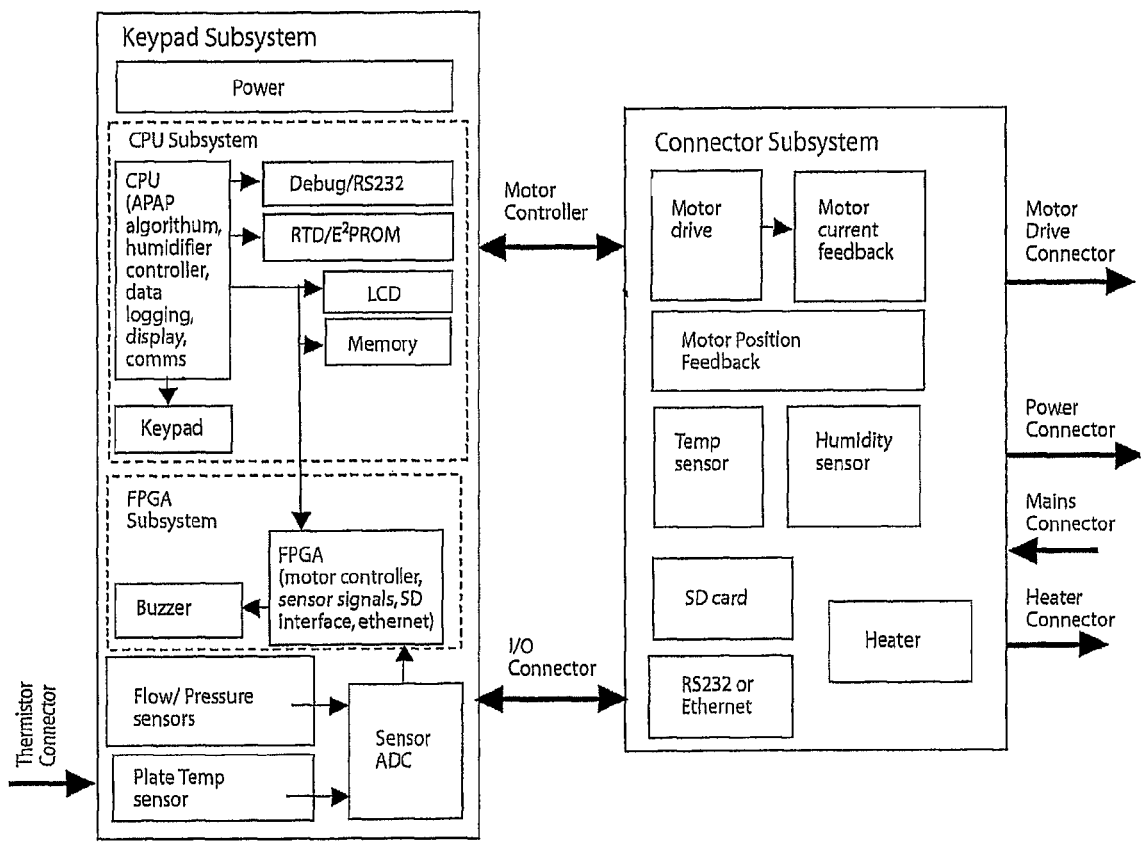
FIG. 7 shows the functional building blocks of the electronic sub-system, of a gas delivery device having a keypad for controlling the operation.
Figure 8:
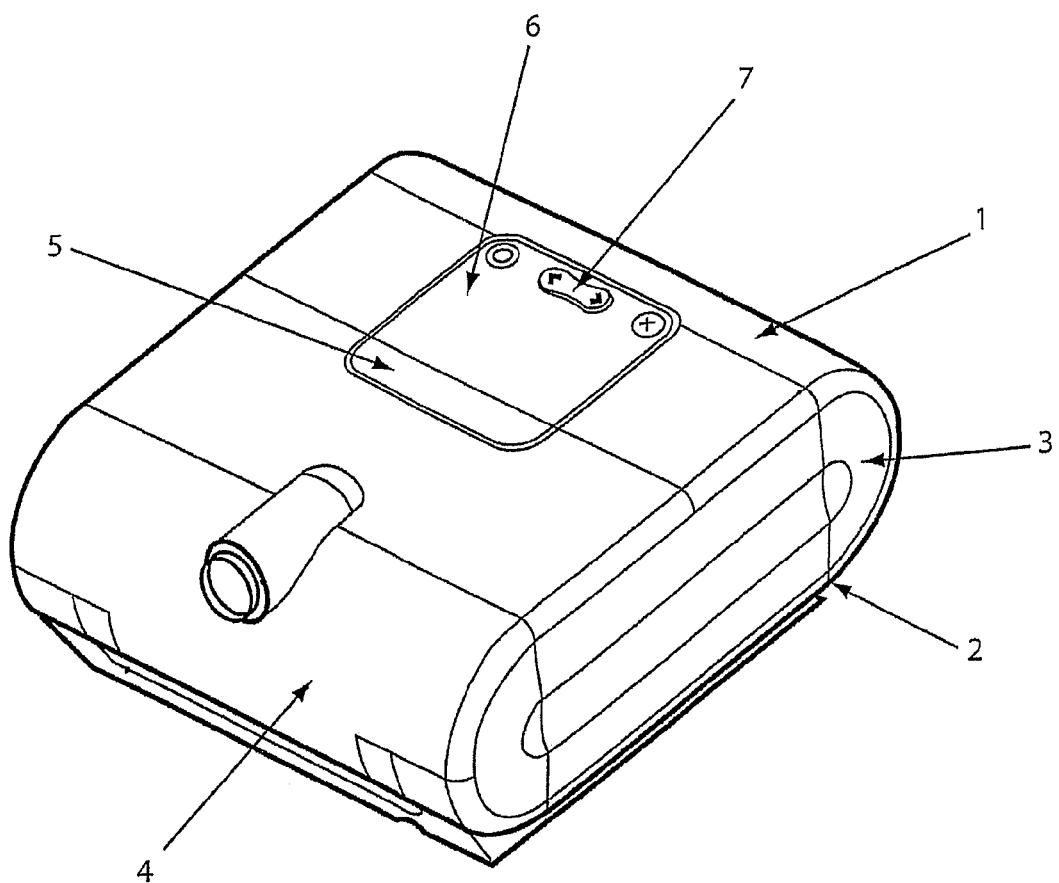
FIG. 8 shows a perspective view of a gas delivery device.

The invention incorporates two printed circuit boards (PCBs), configured as shown in FIG. 7.

The CPU Block is responsible for:

The APAP algorithm

The Humidifier controller

Data logging

Visual display

Audio tones

High level data communication

The Memory Block consists of computer memory.

The LCD Block contains an LCD display, preferably with a white LED. It is used to provide visual feedback to the user. The RTC uses a real-time clock chip. It will have backup power for data retention. In addition to keeping time, the clock is also used to maintain state information about the gas delivery device so that operation can be recovered in the event of a power failure. The EEPROM stores the calibration data for the unit. Both of these devices communicate with the CPU Block.

The Debug/RS232 Block contains the necessary interface connector/logic for an Ethernet or RS232 transceiver for diagnostic and control purposes.

The Keypad block includes four LED backlit buttons to control the unit. The buttons are arranged in a row. One button may function as both an on/off switch and mode selection button. The other buttons are option selection buttons.

The FPGA Block includes the following functionality:

The motor controller

A CPU interface for the sensor signals (flow, pressure, ambient temperature, plate temperature and humidity)

A CPU interface for the SD card

CPU interface for the Ethernet Controller

A CPU interface and controller for the Buzzer block

The Buzzer Block is used to provide auditory feedback for button presses and alarms.

The Sensor ADC includes analogue-to-digital conversion for the flow, pressure and plate temperature sensor signals. The pressure sensor measures the pressure of the generated airflow. A differential pressure technique is used to measure the rate of airflow. It includes, plate temperature feedback for the humidifier controller. The power supply takes a DC input and generates four voltages. The Heater Block contains the switching mechanism and isolation for the control of the humidifier heater plate. The SD Card Block consists of a SD Card holder and necessary logic to interface the FPGA Block to a SD Card. The RS232 or Ethernet Block contains either a connector for either serial or LAN connection.

The invention includes that the FPGA controls the operation of the motor. The CPU interface allows a microprocessor to control the FPGA. The Decoder is a standalone block that performs chip selection for the interface. The Sensor ADC Interface performs a serial to parallel conversion. The interface reads channels and stores the result in registers accessible via the CPU Interface. The Temperature interface performs a serial to parallel conversion for a temperature sensor. The temperature is stored in a register accessible via the CPU Interface. The Humidity Interface performs a period measurement on the humidity signal from the Main PCB of the gas delivery device. The result is accessible via the CPU Interface. The buzzer controller generates a square wave signal for driving a buzzer, preferably a piezo buzzer. The frequency and duty cycle are programmable via the CPU Interface.

The Card Controller includes read and write buffering for accessing the card on the gas delivery device. It is designed to relieve processing from the processor.

Description of Software/Firmware

The invention includes firmware that is a pre-emptive multitasking system.

The main parts to the gas delivery device firmware include:
The Kernel
The Fault task
The Auto CPAP algorithm
The Humidifier task.
The SD Card task.
The Command task.
The Communications task.
The Display task.
The Watchdog task.
The FPGA Download functions.
The Firmware Upgrade functions.
The Real-Time Clock functions.
The EEPROM Functions.

The Kernel is the underlying OS that co-ordinates the swapping between tasks and handles low-level tasks such as interrupt handling and QSPI access. The Fault task is the highest priority task. It functions to monitor the motor for fault conditions and to then take appropriate actions to shutdown and report the fault. The Humidifier task functions to control the humidifier heater. It controls how much power is applied to the heater to produce a certain amount of humidity, based on the current ambient temperature and humidity. The SD Card task logs data produced by the algorithm, fault and humidifier tasks to a SD card. The Command task is a basic monitor program that allows the invention to be controlled via a serial port or a 10/100 Ethernet port. The Communications task will either control a serial port or 10/100 Ethernet port. The Display task controls the LCD and buzzer. It also provides the alarm/clock functionality for the unit. The remaining four parts include sets of utility functions that provide access to various parts of the gas delivery device. These include the FPGA downloading, real-time clock interfacing, $E^EPROM$ access and FLASH/Firmware reprogramming.

TABLE I

| | Acronyms used in this document |
|---|---|
| CPU | Central Processing Unit |
| $E^2PROM$ | Electrically Erasable Programmable Read Only Memory |
| EMI | Electro-magnetic Interference |
| FET | Field Effect Transistor |
| FPGA | Field Programmable Gate Array |
| LCD | Liquid Crystal Display |
| LED | Light Emitting Diode |
| LVCMOS | Low Voltage Complementary Metal Oxide Semiconductor |
| MOSFET | Metal Oxide Semiconductor Field Effect Transistor |
| PWM | Pulse Width Modulation |
| RTC | Real Time Clock |
| SPI | Serial Peripheral Interface |

The invention claimed is:

1. A method for controlling a motor of a blower in a gas delivery device, the method being performed by a microcontroller to include the steps of:
    determining a rotational position of an impeller connected to a rotor at a plurality of locations in a rotation of the impeller using a single rotor position sensor which generates rotor position data, wherein the rotor position data is normalized for determining a rotation period of the rotor,
    determining a velocity of the impeller, and
    adjusting a timing of winding excitations for controlling a speed of the impeller.

2. A method for delivering breathable gas to a subject, the method including the steps of:
    pressurising ambient gas with an impeller connected to a rotor,
    humidifying the ambient gas; and
    directing the humidified gas to an airway of a subject;
    wherein the pressurising step include as performed by a microcontroller, controlling a rotation of the impeller from rotor position data detected by detecting a position of the impeller at a plurality of locations in a rotation of the impeller with a single rotor position sensor, wherein the rotor position data is normalized for determining a rotation period of the rotor.

3. The method of claim 2 wherein the single rotor position sensor is a Hall effect sensor.

* * * * *